(12) United States Patent
Fiz

(10) Patent No.: US 6,179,838 B1
(45) Date of Patent: Jan. 30, 2001

(54) BONE FIXATION ARRANGEMENTS AND METHOD

(76) Inventor: Daniel Fiz, Washington 2242, 1430 Capital Federal (AR)

( * ) Notice: Under 35 U.S.C. 154(b), the term of this patent shall be extended for 0 days.

(21) Appl. No.: 09/028,242

(22) Filed: Feb. 24, 1998

(51) Int. Cl.$^7$ ................................................ A61B 17/70
(52) U.S. Cl. .............................................. 606/61; 606/73
(58) Field of Search .................. 606/60, 61, 72, 606/73

(56) References Cited

U.S. PATENT DOCUMENTS

| | | |
|---|---|---|
| 4,257,409 | 3/1981 | Bacal et al. . |
| 4,483,334 | 11/1984 | Murray . |
| 4,611,580 | 9/1986 | Wu . |
| 4,648,388 | 3/1987 | Steffee . |
| 4,719,905 | 1/1988 | Steffee . |
| 5,000,165 | 3/1991 | Watanabe . |
| 5,053,034 | 10/1991 | Olerud ................................... 606/61 |
| 5,084,049 | 1/1992 | Asher et al. ........................... 606/61 |
| 5,129,900 | 7/1992 | Asher et al. ........................... 606/61 |
| 5,254,118 | 10/1993 | Mirkovic ................................ 606/61 |
| 5,306,275 | 4/1994 | Bryan ..................................... 606/61 |
| 5,312,404 | 5/1994 | Asher et al. ........................... 606/61 |
| 5,344,422 | 9/1994 | Frigg ...................................... 606/61 |
| 5,380,325 | 1/1995 | Lahille et al. ......................... 606/61 |
| 5,403,314 | 4/1995 | Currier .................................. 606/61 |
| 5,468,241 | 11/1995 | Metz-Stavenhagen et al. ....... 606/61 |
| 5,474,551 | 12/1995 | Finn et al. ............................. 606/61 |
| 5,476,463 | 12/1995 | Boachie-Adjei et al. ............. 606/61 |
| 5,487,744 | 1/1996 | Howland ............................... 606/61 |
| 5,496,321 | 3/1996 | Puno et al. ............................ 606/61 |
| 5,498,262 | 3/1996 | Bryan ..................................... 606/61 |
| 5,522,816 | 6/1996 | Dinello et al. ........................ 606/61 |
| 5,527,314 | 6/1996 | Brumfield et al. .................... 606/61 |
| 5,545,228 | 8/1996 | Kambin ................................. 623/17 |
| 5,562,661 | 10/1996 | Yoshimi et al. ....................... 606/61 |
| 5,562,662 | 10/1996 | Brumfield et al. .................... 606/61 |
| 5,609,592 | 3/1997 | Brumfield et al. .................... 606/61 |
| 5,624,442 | 4/1997 | Mellinger et al. .................... 606/61 |
| 5,645,544 | 7/1997 | Tai et al. ............................... 606/61 |
| 5,651,789 | 7/1997 | Cotrel .................................... 606/61 |
| B1 4,648,388 | 10/1995 | Steffee ................................... 606/61 |
| B1 4,719,905 | 10/1995 | Steffee ................................... 606/61 |

Primary Examiner—Michael Buiz
Assistant Examiner—David O. Reip
(74) Attorney, Agent, or Firm—Carella, Byrne, et al.; John G. Gilfillan, III; William Squire (57) ABSTRACT

A bone fixation device, e.g., a pedicle screw or hook, having a threaded head is secured to a rod by a coupler comprising a pair of elements, one having a bifurcated body with rod receiving bores and a flange with a bore for receiving the threaded head. A second element has a body between the bifurcated body portions hinged to the other element by a pivot pin. A flange with a head receiving bore extends from the second element body juxtaposed and aligned with the other element flange bore. The second element body has a rod receiving bore offset relative to the rod receiving bores of the body portions. A nut screwed to the head clamps the overlying pivoting flanges together clamping the pivoting offset rod bores to the received rod. In a second embodiment, the second element body is a hook. The hook and body portions form offset rod receiving openings pivoting about the received rod and which clamp the rod when the flanges are clamped together via the nut and head. A guide rod screwed to an internal bore of the head of a fixation device secured to a bone to be corrected guides a nut and wrench for attachment of the nut to the head, displacing the bone toward the rod fixed position during tightening.

14 Claims, 6 Drawing Sheets

BONE FIXATION ARRANGEMENTS AND METHOD

This invention relates to bone fixation apparatus for immobilizing the spine, and more particularly, to apparatus of posterior internal fixation of the spine and to a method for affecting such fixation.

Spinal fixation apparatuses are widely employed in surgical processes for correcting for spinal injury and diseases. These apparatuses employ longitudinal link rods secured to coupling elements which elements in turn are secured to the bone such as vertebrae by spinal bone fixation fasteners such as pedicle screws, hooks and others. Transverse bridge elements connect parallel rods which extend along the spinal column, the rods being connected by the bridge elements to opposing sides of the spinal column portion being corrected. These apparatuses are supplied for posterior internal use and require flexibility in surgical implantation to facilitate the surgery and maximize the corrective action with minimum patient discomfort.

U.S. Pat. No. 5,522,816 to Dinello et al. discloses an apparatus for interconnecting a pair of longitudinal members for fixation to vertebrae including connector members connected to the longitudinal members. An elongate plate extends transverse to the longitudinal members and interconnects the connector members. A set screw clamps a hook to a longitudinal member. A nut engages the set screw to clamp the plate to the connector member. The plate has a recess for receiving the connector member to prevent pivoting of the elongate member.

U.S. Pat. No. 5,624,442 to Mellinger et al. discloses a transverse connector member to connect two parallel spinal implant rods. The connector member includes a clamp comprising a rod receiving recess and a top-loaded set screw which causes a horizontal and vertical loading of the rod to bias the rod into contact with the recess. In one embodiment, an adjustable distance is provided between clamping members. In another embodiment, the connector is a single unit in which the clamping members have openings in the same direction to facilitate loading the connector onto the rods.

In U.S. Pat. No. 5,380,325 to Lahille et al. a consolidation rod, pedicle screws and vertebrae claws are disclosed with threaded sections fitted with a nut for clamping to the rod. The fastener comprises a first bore sliding on the rod, a first opening into the first bore and narrowed by nut screwing, and a second bore passing through the slit and passed through by the threaded section. An indented plate, or a bar with threaded ends fitted with hooks transversely stabilizes the two consolidation rods. A connector longitudinally stabilizes the two consolidation rods.

U.S. Pat. No. 5,466,241 discloses a further support device for a human vertebrae column. The head of two pedicle screws are mounted on a holding device pivotally about an axis normal to the screw shank axis. A securing device fixes the screws in a fixed angular position and at desired axial intervals, the holding device including two bolts cooperating with a threaded sleeve including a clamping surface. For each bolt a screw connection is provided which clamp fixes with respect to each other in their position the clamping surfaces of the bolts and pedicle screws or of the two bolts.

U.S. Pat. No. 5,651,789 to Cotrel discloses two fixation hooks which move along a rigid bar in sliding manner and are equipped with means for locking on the bar. A body has a hook extending therefrom. The body has a first bearing surface for engaging a first elongate member. The first surface conforms to a portion of the elongate member outer surface. The body has a second bearing surface transverse the first surface. The first bearing surface which abuts a portion of a second elongate member when the second elongate member is transverse to the first elongate member. A plug bears against the second elongate member to clamp the second elongate member against the first elongate member when the first elongate member is engaged with the first bearing surface.

Still other fixation devices are disclosed in U.S. Pat. Nos. 5,498,262, 4,483,334, 5,254,118, 5,306,275, 5,344,422, 4,474,551, 5,645,544, 5,129,900, 4,648,388, 4,719,905, 5,000,165, 5,053,034, 5,084,049, 5,129,900, 5,312,404, 5,344,422, 5,487,744, 5,545,228 and 5,562,661. These all disclose various arrangements of couplers and fixation devices for securing a bone fixation element to an elongated bone fixation rod.

The present invention is in recognition of a need for a bone fixation coupler and bone fixation assembly method that uses a minimum of components and is simple to implement.

A bone fixation coupler according to the present invention for securing a bone fixation link rod to a bone fixation member comprises first and second elements each having a body and a flange extending from the body, the bodies and flanges being juxtaposed and secured for relative pivoting displacement, the bodies each having an opening for receiving the rod on an axis, the openings being offset relative to each other along the axis in the juxtaposed relation. The juxtaposed flanges have aligned bores for receiving a portion of the fixation member, the received member portion for clamping the juxtaposed flanges together, the offset openings being dimensioned relative to the flanges and to each other for clamping the received rod to the bodies in response to the clamping of the flanges.

In one aspect, the opening in one body is a circular cylindrical bore and the opening in the other body is a hook.

In another aspect, each body has a further bore and further includes a pivot pin in the further bore of each body for hinging the elements about the pivot pin.

In another aspect, the body of one of the elements is bifurcated forming a slot, the body of the other of the elements being located in the slot.

In a further aspect, the flanges of each element are planar and parallel to a first plane, the bodies each being planar and parallel to a second plane, the first and second planes being normal.

In a further aspect, the bone fixation device comprises a bone fixation member having opposing first and second ends and includes first means for fixation to a bone at the first end and second means for receiving a fastener at the second end. Tool guide receiving means are at the second end for receiving a tool guiding device for guiding a tool for fastening the fastener to the second means. Securing means are intermediate the ends and cooperate with the fastener for securing the element to a link rod coupling device. A tool guide is secured to the tool guide receiving means.

In a further aspect, the guide receiving means is a threaded bore and the guide is an elongated shaft.

In a further aspect, the second end has external threads and the fastener is a nut mating with the threads.

In a further aspect, the first means comprises one of a threaded shank and hook for engaging a bone.

A method of attaching a link rod to a bone fixation element according to an aspect of the present invention comprises securing the link rod in fixed spaced relation to a bone; attaching a bone fixation member to the bone; attaching a coupler element to the link rod; and guiding and simultaneously fastening a fastener to the bone fixation member and to the coupler while simultaneously pulling the fixation member and the bone toward the link rod and coupler during the fastening.

Figure 1:
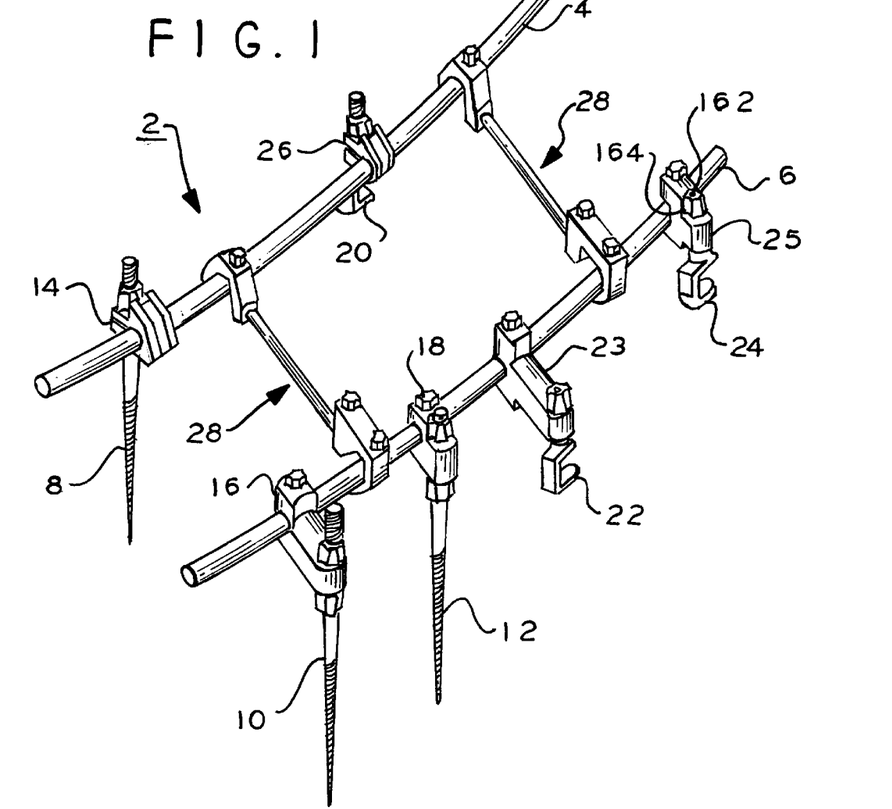
FIG. 1 is an isometric view of a bone fixation assembly for fixation to a spinal column (not shown)

In FIG. 1, bone fixation assembly 2 is for attachment to vertebrae of a spinal column (not shown). The assembly 2 includes two generally parallel link rods 4 and 6, preferably stainless steel and circular cylindrical. The rods 4 and 6 may be straight or bent according to a given implementation to conform to a spinal column to which the assembly 2 is attached. The rods 4 and 6 rigidify the column in a known way by surgical implantation in the posterior region of the column.

A plurality of pedicle screws 8, 10 and 12 are embedded in and fixed to corresponding pedicles of the spinal column in a known manner. Screw 8 is attached to rod 4 by coupler 14. Screw 10 is attached to the rod 6 by coupler 16. Screw 12 is attached to rod 6 by coupler 18. By way of example, three identical bone hooks 20, 22 and 24 which may be different according to a given implementation, are secured to the spinal column in a known manner. Hook 20 is secured to rod 4 by coupler 26. Hooks 22 and 24 are secured to rod 6 by respective couplers 23 and 25. Two bridge assemblies 28 fix rod 4 to rod 6.

In FIGS. 2–8, coupler 14 comprises two elements 30 and 32, preferably formed of stainless steel. Element 30 comprises a body 33 formed of identical bifurcated spaced body portions 34 and 36 from which extends a flange 38 which interconnects the body 33 portions 34 and 36 to form a one piece rigid structure. The body 33 portions 34 and 36 are mirror images of each other and are spaced a gap 37.

Figure 2:
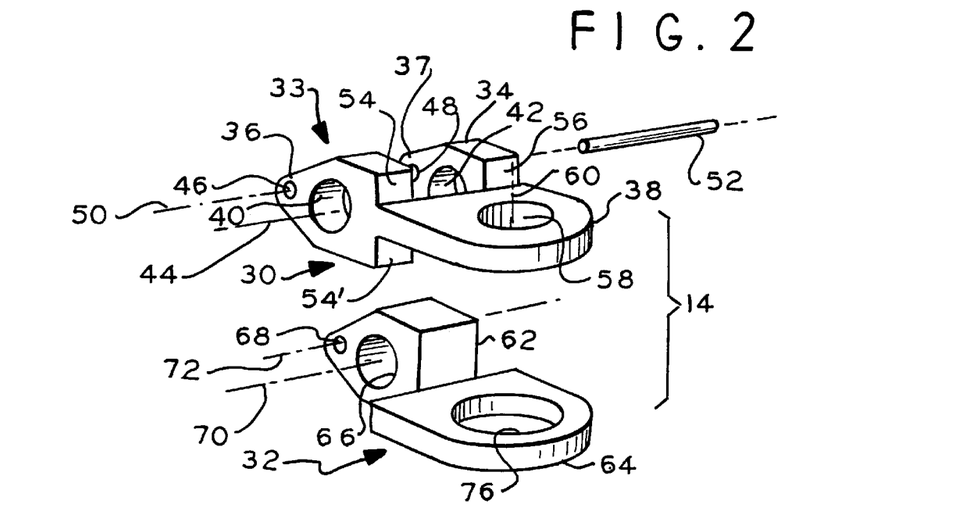
FIG. 2 is an exploded view of a coupler according to an embodiment of the present invention employed in the assembly of FIG. 1.

Each portion has a respective circular cylindrical through bore 40, 42 which receive rod 4 (FIG. 6) on axis 44. The bores 40 and 42 are identical, but are larger in diameter than the rod 4 outer diameter. A second smaller diameter through bore 46, 48 is in a corresponding respective body portions 34, 36 aligned on axis 50. The bores 46 and 48 receive pin 52 on axis 50 such that element 30 can pivot about pin 52 on axis 50.

The body portions 34 and 36 each have a somewhat triangular rear wall and respective shoulders 54, 56 formed by front end faces adjacent to the flange 38 where it extends from the body portions 34, 36. The shoulders extend normal to above and beneath the plane of the flange. The flange 38 extends generally medially from the shoulders 54 and 56 which generally have the same extent from the flange 38. The portions 34 and 36 are generally planar and lie in planes normal to the axis 44 and to the plane of flange 38 which is also planar. The flange 38 has a through bore 58. Bore 58 lies on axis 60 lying in a plane that is normal to axes 44 and 50.

Element 32 has a body 62 lying in one plane and a flange 64 lying in a second plane normal to the plane of body 62. The body 62 has a width slightly less than the width of the gap 37 of element 30 for being received in the gap. The body 62 has a through bore 66 on axis 70 and a through bore 68 on axis 72. Bore 66 is larger in diameter than the rod 4 and preferably is about the same diameter as the diameter of bores 40 and 42 of element 30. The bore 68 has a diameter that is preferably identical to the diameter of bores 46 and 48 of element 30 for receiving pivot pin 52 on axis 72. The body 62 has a transverse width along axis 70 for being received in the space between the body portions 34 and 36 of element 30, FIG. 3.

Figure 3:
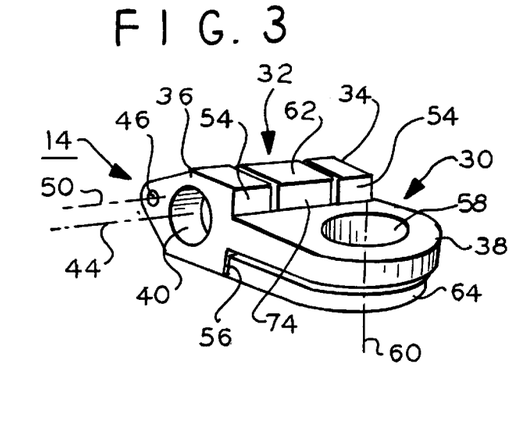
FIG. 3 is an isometric view of an assembled coupler of FIG. 2.
Figure 4:
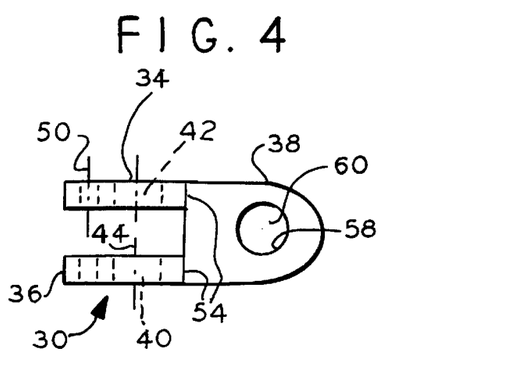
FIGS. 4 and 5 are respective plan views of the coupler elements of FIG. 2.

The body 62 has a face 74 that is coextensive with the faces of shoulders 54, 56 of element 30 with pin 52 through the body 62 bore 68 and the aligned body portion bores 46, 48 of element 30. The flange 64 has a through bore 76 which axially aligns with bore 58 of element 30 when the two flanges are juxtaposed assembled as shown in FIG. 3. The two through bores 58 and 76 are complementary shaped to receive therethrough the frusto-conical shank 8' of a pedicle screw 8 or corresponding shank of another element such as a hook 78 (FIG. 21) or hook 80 (FIG. 22) (as will be explained below). The body 62 face 74 abuts or is adjacent to the flange 38 of element 30 in the assembled state, FIG. 3. The flanges 38 and 64 have complementary thicknesses to accommodate the clamping function described below.

Figures 5, 6, 7, 8:
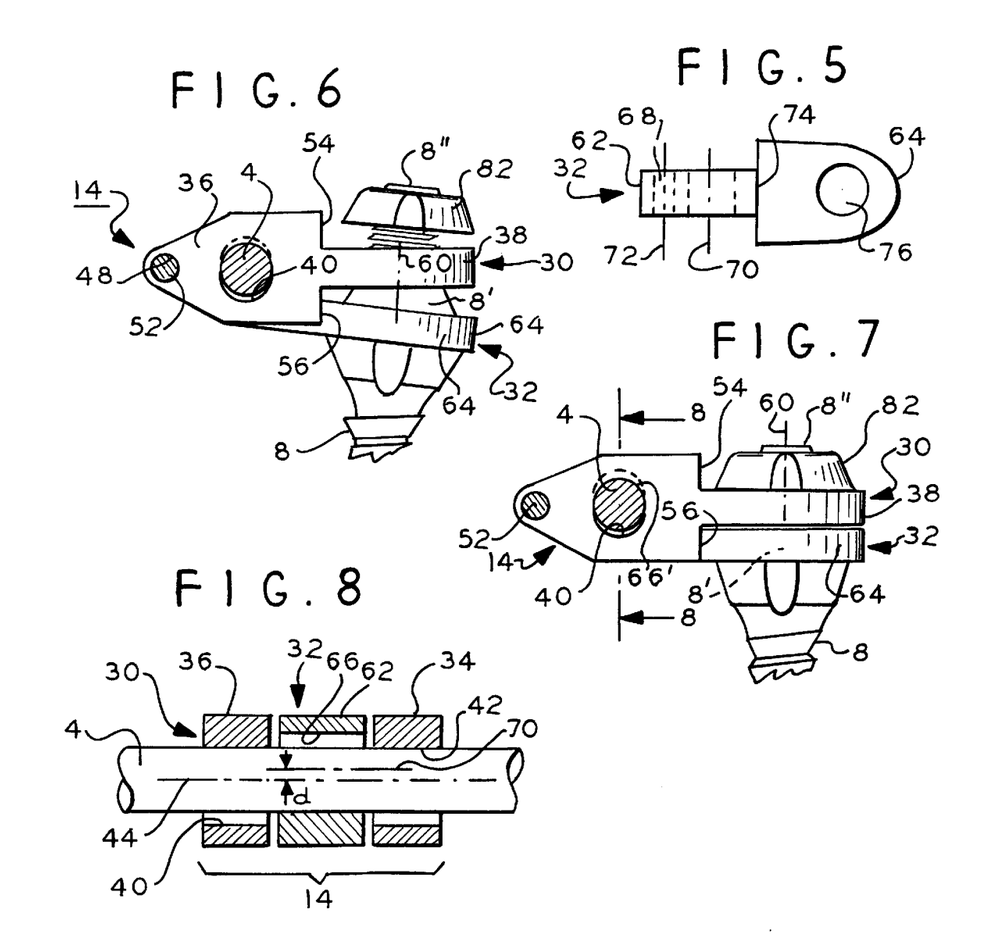
FIGS. 6 and 7 are respective elevation side views of the coupler of FIG. 2 during after assembly to an elongated fixation link rod.
FIG. 8 is a sectional elevation view of the coupler of FIG. 7 taken along lines 8—8.

In the assembled state of FIG. 3 with the pin 52 passing through the bores 46, 48 and 68, the bores 40 and 42, preferably circular cylinders, of element 30 are offset relative to the preferably circular cylindrical bore 66 of element 32 with the flanges 38 and 64 juxtaposed in facing parallel relation, FIGS. 3 and 7. In FIG. 8, the axis 44 of bores 40 and 42 is offset distance d from axis 70 of element 32 bore 66. Distance d may be about 2–mm, for example.

In operation, the pin 52 is assembled to the bores 46, 48 and 68 of respective elements 30 and 32 forming a hinge for the elements about substantially coaxial axes 50 and 72, FIGS. 2 and 3. The pedicle screw 8 shank 8' is passed into and through the flanges 38 and 64 respective bores 58 and 76, FIG. 6. In this position, the flange 64 is tilted somewhat relative to the flange 38.

The pedicle screw has a machine threaded shank 8" which passes through the bores of the flanges and protrudes upwardly therefrom, FIGS. 6 and 7. A nut 82 is attached to the shank 8" end and tightened. As the nut 82 is tightened, it forces the flanges 38 and 64 of the two elements together, FIG. 7. This clamps the rod 4 to the body portions 34 and 36 bores 40 and 42 on one side of these bores and to the body 62 bore 66 on the opposite side of bore 66 as shown in FIG. 8. With the flanges 38 and 64 clamped together as shown in FIG. 7, the offset bores 40, 42 and 66 engage and clamp the rod thereto due to their axially misalignment without further fasteners.

Figure 9:
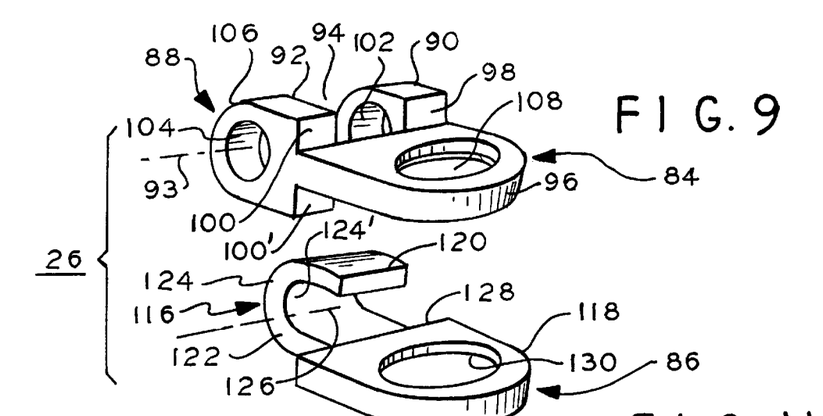
FIG. 9 is an exploded view of a coupler of FIG. 2 according to a second embodiment.

In FIG. 9, a second embodiment of a coupler 26 comprises elements 84 and 86. Element 84 has a bifurcated body 88 comprising body portions 90 and 92 spaced apart a gap 94. A flange 96 extends from the end faces of body portions 90 and 92 forming shoulders 98, 100. The portions 90 and 92 have preferably circular cylindrical through bores 102, 104, respectively, axially aligned on and concentric with axis 93. The bores 102, 104 are the same diameter but are larger than the outer diameter of link rod 4, FIG. 1, for receiving the rod therethrough. The portions 90 and 92 are generally planar with a curved external rear wall 106 and are mirror images of each other.

Figure 13:
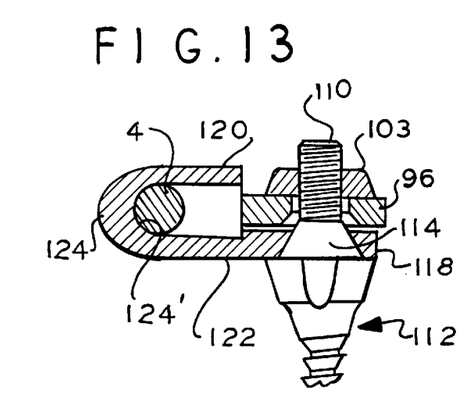
FIG. 13 is a side elevation sectional view of the coupler of FIG. 10 further including a pedicle screw fastened thereto.

The flange 96 is planar and lies in a plane normal to the plane of the body 88 portions. A through bore 108 dimensioned to receive the upper externally threaded shank 110 of a pedicle screw 112 (FIG. 13). The bore 108 may be partially cylindrical and partially frusto-conical to mate with the shank of screw 112 frusto-conical portion 114. The flange 96 may have any desired thickness according to a given implementation for the purpose to be described below which purpose is similar to that of the flange 38 of the embodiment of FIG. 2.

The element 86 comprises a hook shaped body 116. A planar flange 118 extends from the body 116. The body 116 comprises two generally parallel legs 120 and 122 connected by and extending from a circular segment 124. The segment 124 and legs form an open sided through bore 124' having a longitudinal axis 126. The segment comprises a portion of a circular cylinder having a diameter about the same as the diameter of the bores 102, 104. The legs 120 and 122 are thus spaced apart a distance of the diameter of the bores 102, 104.

The flange 118 extends coextensive and coplanar with the leg 122 and is thicker than leg 122. The flange 118 has a shoulder 128 at the junction with the leg 122. A through bore 130 is in flange 118. The bore 130 accommodates the pedicle screw 112 frusto-conical shank 114, FIG. 13.

The body 116 of element 86 in use is disposed in the gap 94 between the body portions 90 and 92 of element 84. The body 116 has a clearance to be able to displace in the gap 94. The rod 4 is passed through the bores 102 and 104 of the respective body portions 90 and 92.

Figure 10:
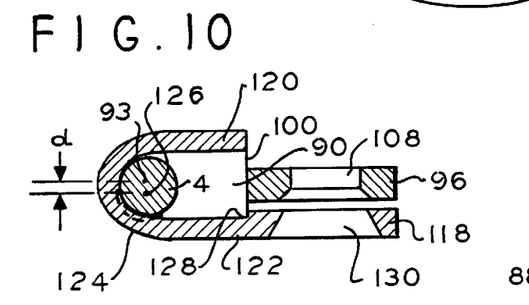
FIG. 10 is a sectional side elevation view of the coupler of FIG. 9 assembled to an elongated link rod.
Figure 11:
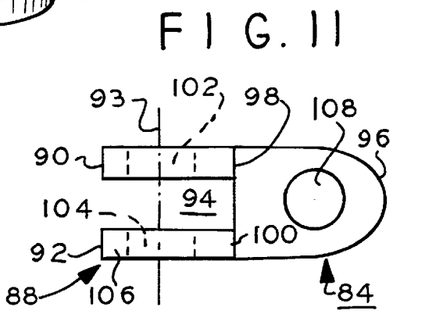
FIGS. 11 and 12 are respective plan views of the elements of FIG. 9.
Figure 12:
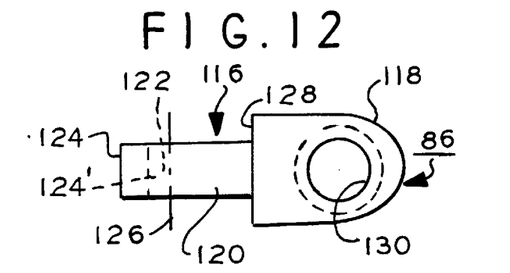
Figure 13A:
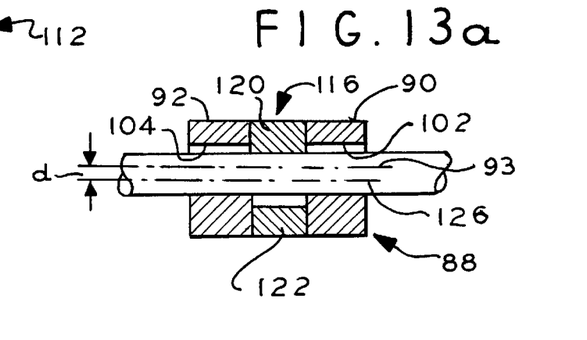
FIG. 13a is a sectional elevation view through the assembled coupler of FIG. 9 including a link rod.

The axis 93 of the bores 102, 104 of the body portions and axis 126 of the segment 124 bore 124' are misaligned by preferably about 2–4 mm distance d, FIG. 13a, when the respective flanges 96 and 118 of the elements 84, 86 are juxtaposed in the position of FIGS. 10 and 13a. This misalignment causes the rod 4 to be clamped by leg 120 and body portions 90 and 92, FIG. 13a as the flanges 96 and 118 are forced toward each other by the attached pedicle screw 112 in the flange bores 108 and 130, FIGS. 13 and 13a. As the nut 103 is tightened the flanges are forced together. This clamps the body portions and body of the elements of coupler 26 to the rod 4. This is similar to the clamp action of the coupler 14 of FIG. 2.

Figure 14:
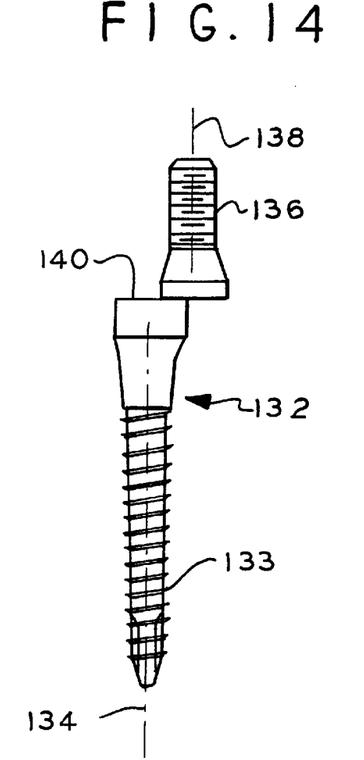
FIG. 14 is an elevation view of an offset pedicle screw which may be used in the embodiment of FIG. 1.

FIGS. 14–19 illustrate different components that may be employed with the assembly of FIG. 1, and in particular, may be connected to the link rods 4 and 6. In FIG. 14, an offset pedicle screw 132 includes a helically bone fixation threaded shank 133 having an axis 134. A threaded head 136 has an axis 138 offset from the axis 134. Shoulder 140 and head 136 receive a coupler such as any of the couplers of FIG. 1.

Figure 15:
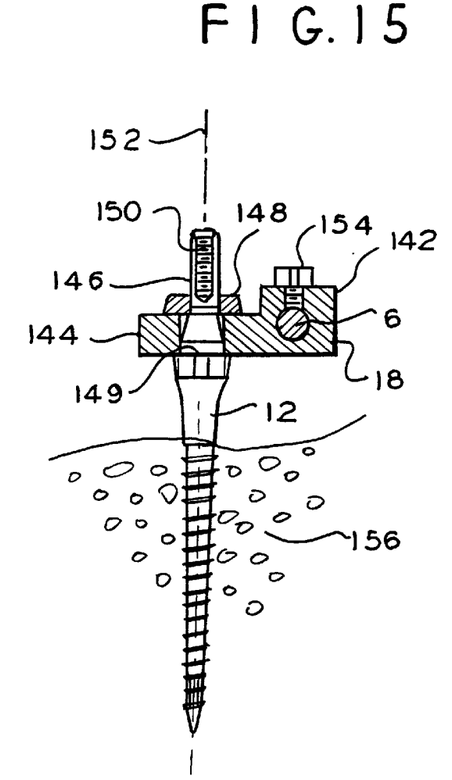
FIG. 15 is an elevation view of a pedicle screw and coupler according to an aspect of the present invention.

In FIG. 15, pedicle screw 12 and coupler 18 are shown in more detail. The coupler 18 is L-shaped with a body 142 and a flange 144. The screw head 146 is attached to the flange 144 by a nut 148 and a screw shoulder 149. The head 146 has an internal threaded bore 150 on axis 152. The bore 150 serves to permit attachment of the coupler 18 to the screw 12 as will be described in connection with FIGS. 19a, 19b and 19c.

The coupler 18 is attached to rod 6 by screw 154. The screw 12 is inserted into bone 156 in a known manner. The nut 148 then clamps the screw 12 to the coupler 142.

Figure 16:
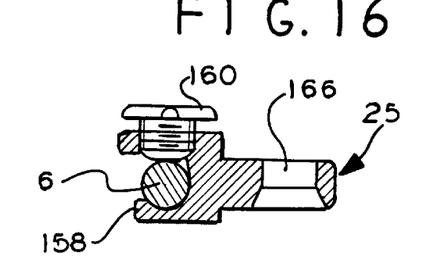
FIGS. 16–18 are sectional elevation views of couplers employed in the embodiment of FIG. 1.

FIG. 16 illustrates coupler 25 for use with a bone hook 24 (FIG. 1). Coupler 25 has a bifurcated portion 158 for receiving rod 6 which is attached thereto by screw 160. The hook 24, FIG. 1, has a threaded head 162 which is secured to the coupler 25 by nut 164.

Figure 17:
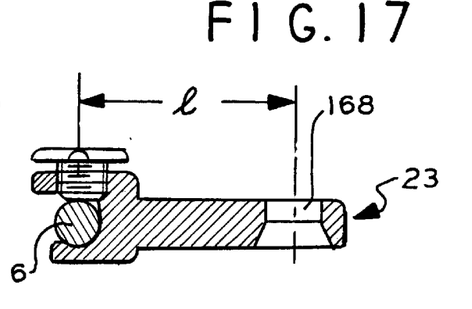

FIG. 17 illustrates coupler 23 which is similar to coupler 25 except it has a length 1 between the pedicle screw bore 168 and the rod 6 axis greater than that of the coupler 25. The bores 166 and 168 of respective couplers 23 and 25 receive either the shank of a bone hook or a pedicle screw as needed for a given implementation. The bores 166 and 168 in the couplers 23 and 25 receive the heads of hooks 22 and 24, FIG. 1.

Figure 18:
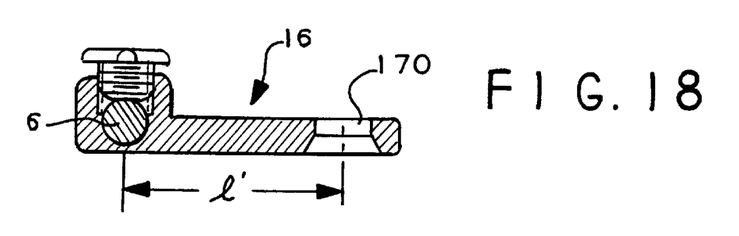

In FIG. 18, the coupler 16 has a length 1' between the pedicle screw bore 170 and the rod 6 axis that is greater than the corresponding length of the coupler 18, FIG. 15 which otherwise is the same.

Figures 19A, 19B, 19C, 20:
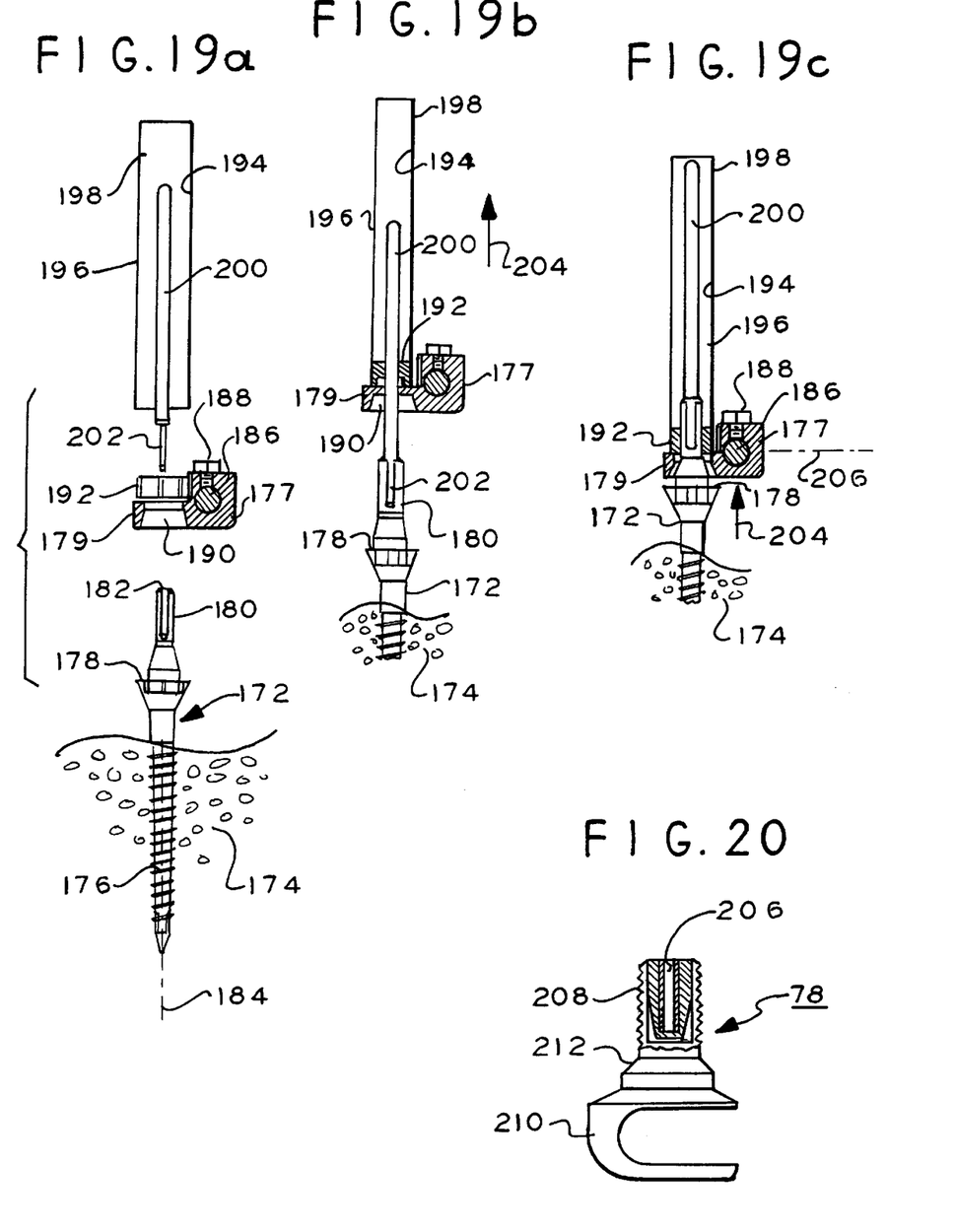
FIGS. 19a, 19b and 19c are elevation views of a method and apparatus for attaching a bone fixation element to an elongated link rod.
FIG. 20 is a side elevation partially in section of a bone fixation element for use with the method of FIGS. 19a–19c.

In FIGS. 19a–19c, a method for attaching a pedicle screw 172 to a bone 174 is shown. The pedicle screw 172 has a threaded bone fixation threaded shank 176 that is embedded in the bone 174. The screw 172 has a coupler 177 support shoulder 178. The shoulder receives and supports the flange 179 of the coupler 177. The screw 172 has an externally threaded head 180 extending from the shoulder 178.

A threaded bore 182 is in the head 180 on the screw axis 184. The coupler 177 is fixed to a link fixation rod 186 by screw 188. The coupler 177 has a bore 190 for receiving the head 180. In practice the coupler bore 190 is engaged somewhat with the head 180 after the screw 172 is attached to the bone. The spacing between the coupler and the pedicle screw 172 is exaggerated in the drawing for purposes of illustration.

A nut 192 for engaging the external threads of the head 180 is placed on the flange 179 aligned over the bore 190. The nut 192 has a polygon or other faceted exterior surface. The exterior surface receives a keyed mating core 194 of a tubular elongated preferably metal wrench 196 having an externally faceted handle 198, FIG. 19b. An elongated guide rod 200 has a threaded tip 202 which is temporarily engaged with the threaded bore 182 of the head 180, FIG. 19b.

It should be understood that in FIG. 19b the coupler 177 bore 190 in practice has received the head 180 of the screw 172 at this juncture of the assembly procedure. The coupler flange 179 however is spaced above the shoulder 178 of the pedicle screw 172. The reason for this spacing is due to the bone 174 at this location is deformed relative to other next adjacent bones of the spinal column in this region of the spine. What is desired is to straighten the bone 174 at this location by pulling the bone 174 toward the rod 186, direction 204. The rod 186 and coupler 177 in all of the FIGS. 19a–19c is fixed in the plane 206.

The guide rod 200 guides the nut onto the threaded screw head 180 and permits the surgeon to tighten the nut 192 with the elongated wrench handle 198. As the nut 192 is tightened, the screw action pulls the pedicle screw 172 and the bone 174 toward the plane 206. The guide rod 200, previously attached to the pedicle screw head 180 bore, has an outer diameter that is closely received in the nut 192 threaded bore for guiding the nut onto the screw head 180.

This guiding action provides axial alignment of the nut threads to the screw head 180 threads. This enhances the attachment of the nut 192 threads to the head threads and minimizes crossed threads and the resulting problems of reattaching different nuts and minimizing the possibility of stripping the pedicle screw head 180 threads. Thus the assembly of the pedicle screw of FIG. 15 is facilitated by the guide rod 200 and wrench 198.

Pedicle screws and bone hooks may all be selectively attached to correct a bone deficiency employing the tool of FIGS. 19a–19c. For example, the bone hook 78 of FIG. 20 has a threaded bore 206 in its externally threaded head 208. A bone hook 210 depends from the head 208. A shoulder 212 abuts the flange of a mating coupler. The hook is first attached to a bone to be corrected.

The mating coupler is then attached to the head 208 by engaging the coupler flange bore with the head. The tool guide rod 200 is then attached to the head threaded bore 206. The nut is slipped over the guide rod and the tool 196 slipped over the guide rod 200 and engaged with the nut. The nut is then engaged with the head threads and the hook drawn toward the coupler's fixed position established by the fixation link rod.

Figure 21:
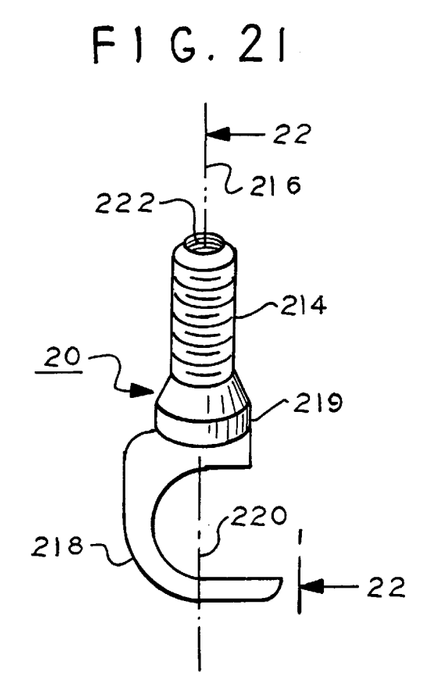
FIG. 21 is a side elevation view of a hook bone fixation element for use with the method of FIGS. 20a–20c.
Figure 22:
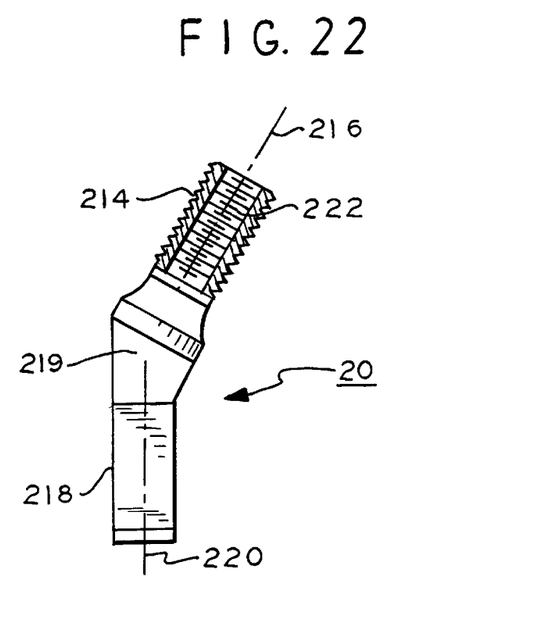
FIG. 22 is an end elevation view partially in section of the hook bone fixation element of FIG. 21 taken along lines 22—22.

In FIGS. 21 and 22, a bone hook 20 has a threaded head 214 on an axis 216 inclined relative to the hook 218 shank 219 axis 220. The threaded head 214 has a threaded bore 222 for receiving the guide rod 200 (FIG. 19a) threaded tip 202. The hook is assembled to its mating coupler 26 (FIG. 1) in a similar manner as described above in connection with the hook 78 of FIG. 20 and screw 172 of FIG. 19a.

Figure 23:
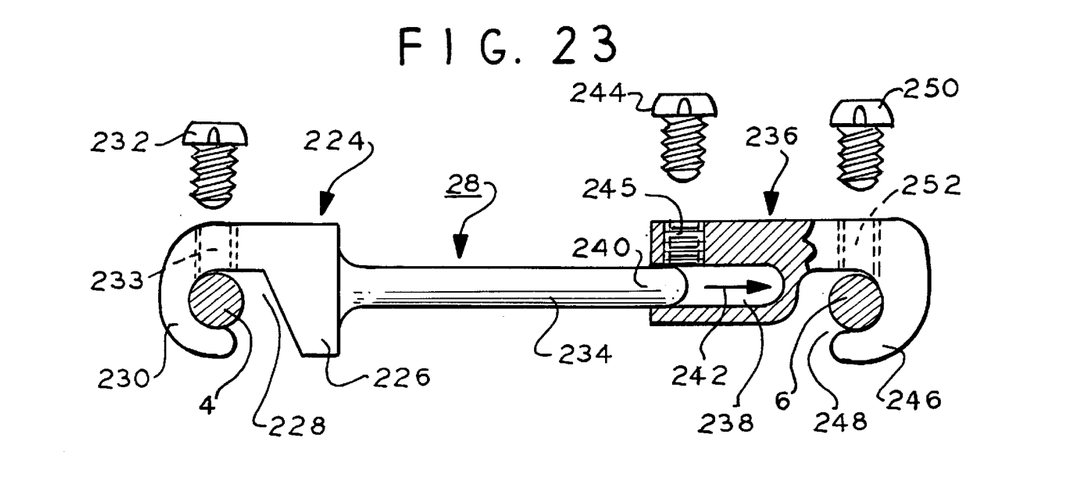
FIG. 23 is a side elevation view partially in section of a transverse link rod connecting bridge employed in the embodiment of FIG. 1.

In FIG. 23, a representative bridge assembly 28 comprises a coupler 224 having a body 226 with a slot 228 for receiving link rod 4. The coupler has a hook 230 coupled to the slot for securing the rod 4 in cooperation with screw 232 via threaded bore 233. A circular cylindrical shaft 234 extends from the body 226.

A second coupler 236 has a circular cylindrical bore 238 for receiving the distal end 240 of the shaft 234 in direction 242. A screw 244 via threaded bore 245 locks the end 240 to the bore 238. The coupler 236 has a hook 246 on one end thereof for receiving rod 6 via slot 248. A screw 150 locks the rod 248 to the hook 246 via threaded bore 252.

It will occur to one of ordinary skill that various modifications may be made to the disclosed embodiments. The disclosed embodiments are given by way of illustration and not limitation. It is intended that the invention be defined by the appended claims.

What is claimed is:

1. A bone fixation coupler for securing a bone fixation link rod to a bone fixation member, said coupler comprising:
   first and second elements each having a body and a flange extending from the body, the bodies and flanges being juxtaposed and secured for relative pivoting displacement, the bodies each having an opening for receiving the rod on an axis, the openings each having rod receiving surfaces offset relative to each other along the axis in said juxtaposed relation;
   said juxtaposed flanges having aligned bores for receiving a portion of the fixation member, said received member portion for clamping the juxtaposed flanges together, said offset surfaces of said openings for cooperatively clamping the received rod to the bodies in response to the clamping of the flanges.

2. The coupler of claim 1 wherein the opening in each body is a circular cylindrical bore.

3. The coupler of claim 2 wherein each said body has a further bore and further includes a pivot pin in the further bore of each body for hinging the elements about the pivot pin.

4. The coupler of claim 2 wherein the rod is a circular cylinder of a given diameter, the bores of said openings are each circular cylindrical and each having a respective diameter greater than that of the rod.

5. The coupler of claim 1 wherein the opening in one body is a circular cylindrical bore and the opening in the other body is a hook.

6. The coupler of claim 1 wherein the body of one of the elements is bifurcated forming a slot, the body of the other of said elements being located in said slot.

7. The coupler of claim 1 wherein the flanges of each element are planar and parallel to a first plane, the bodies each being planar and parallel to a second plane normal to the first plane.

8. A bone fixation device comprising:
   a bone fixation member having a first portion for fixation to a bone and a threaded head for receiving a nut;
   an elongated link rod;
   first and second coupling elements arranged for relative pivoting movement, each element having a body and a flange extending from the body, the bodies and flanges being respectively juxtaposed, each body having an opening defining a first longitudinal axis receiving said rod therethrough, each flange having a bore for receiving said head on a second longitudinal axis normal to the direction of the first axis and in spaced relation to the rod;
   said nut being attached to said head for clamping the flanges together;
   said openings having surfaces offset relative to each other in said juxtaposed relation for cooperatively clamp securing the rod to said bodies in response to said clamping of said flanges.

9. The device of claim 8 wherein the opening in one body is a circular cylindrical bore and the opening in the other body is one of a circular cylindrical opening and a hook.

10. The device of claim 8 wherein each said body has a further bore and further includes a pivot pin in the further bore of each body for pivotally securing the elements about the pivot pin.

11. The device of claim 8 wherein the body of one of the elements is bifurcated forming a slot, the body of the other of said elements being located in said slot.

12. The device of claim 8 wherein the flanges of each element are planar and parallel to a first plane, the bodies each being planar and parallel to a second plane normal to the first plane.

13. The device of claim 8 wherein the rod has a given diameter, the openings comprising bores having respective diameters greater than that of the rod.

14. A bone fixation device for securing a link rod to a bone fixation member comprising:

first coupling means comprising two relatively moving elements for receiving the fixation member in clamping relation thereto; and second coupling means comprising means fixedly secured to said two moving elements for receiving the rod therethrough, said second coupling means having a plurality of relatively movable offset bores for cooperatively clamping the rod thereto in response to the clamping of the fixation member to the first coupling means.

* * * * *